United States Patent
Serhan et al.

(10) Patent No.: US 9,662,149 B2
(45) Date of Patent: May 30, 2017

(54) DYNAMIZED INTERSPINAL IMPLANT

(71) Applicant: DEPUY SYNTHES PRODUCTS, INC., Raynham, MA (US)

(72) Inventors: Hassan Serhan, South Easton, MA (US); Alexander Michel DiNello, Palo Alto, CA (US); William Christianson, Duxbury, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/149,132

(22) Filed: May 8, 2016

(65) Prior Publication Data

US 2016/0249960 A1    Sep. 1, 2016

Related U.S. Application Data

(60) Continuation of application No. 15/149,085, filed on May 7, 2016, which is a continuation of application No. 15/148,937, filed on May 6, 2016, which is a continuation of application No. 14/845,687, filed on Sep. 4, 2015, which is a continuation of application No. 14/134,090, filed on Dec. 19, 2013, now abandoned, which is a division of application No.

(Continued)

(51) Int. Cl.
| | |
|---|---|
| A61B 17/70 | (2006.01) |
| A61F 2/44 | (2006.01) |
| A61B 17/56 | (2006.01) |
| A61B 17/68 | (2006.01) |
| A61B 17/00 | (2006.01) |
| A61F 2/48 | (2006.01) |

(52) U.S. Cl.
CPC ...... *A61B 17/7065* (2013.01); *A61B 17/7062* (2013.01); *A61B 17/7068* (2013.01); *A61F 2/4405* (2013.01); *A61B 2017/00075* (2013.01); *A61B 2017/00221* (2013.01); *A61B 2017/567* (2013.01); *A61B 2017/681* (2013.01); *A61F 2002/482* (2013.01)

(58) Field of Classification Search
CPC ............ A61B 17/7068; A61B 17/7062; A61B 17/707; A61B 17/7064; A61B 17/7067; A61B 2017/681; A61B 2017/567; A61F 2/44; A61F 2/442
USPC ........... 606/246–249, 279; 623/17.11, 17.13, 623/17.15, 17.16
See application file for complete search history.

(56) References Cited

U.S. PATENT DOCUMENTS

| | | |
|---|---|---|
| 3,867,728 A | 2/1975 | Stubstad et al. |
| 4,759,769 A | 7/1988 | Hedman et al. |
| 4,863,476 A | 9/1989 | Shepperd |

(Continued)

FOREIGN PATENT DOCUMENTS

| | | |
|---|---|---|
| DE | 197 10 392 C1 | 7/1999 |
| WO | 00/74605 A1 | 12/2000 |

OTHER PUBLICATIONS

U.S. Appl. No. 15/219,505, filed Jul. 26, 2016, Dynamized Interspinal Implant.

(Continued)

*Primary Examiner* — Pedro Philogene
*Assistant Examiner* — David C Comstock
(74) *Attorney, Agent, or Firm* — Nutter McClennen & Fish LLP

(57) ABSTRACT

An interspinous process having a narrowed distal portion.

17 Claims, 9 Drawing Sheets

Related U.S. Application Data

10/793,967, filed on Mar. 6, 2004, now Pat. No. 8,636,802.

(56) References Cited

U.S. PATENT DOCUMENTS

| | | | |
|---|---|---|---|
| 5,002,576 A | 3/1991 | Fuhrmann et al. | |
| 5,024,670 A | 6/1991 | Smith et al. | |
| 5,071,437 A | 12/1991 | Steffee | |
| 5,123,926 A | 6/1992 | Pisharodi | |
| 5,401,269 A | 3/1995 | Buttner-Janz et al. | |
| 5,458,642 A * | 10/1995 | Beer .................... | A61F 2/4425 606/247 |
| 5,522,899 A | 6/1996 | Michelson | |
| 5,527,312 A | 6/1996 | Ray | |
| 5,645,599 A | 7/1997 | Samani | |
| 5,665,122 A | 9/1997 | Kambin | |
| 5,674,294 A | 10/1997 | Bainville et al. | |
| 5,674,296 A | 10/1997 | Bryan et al. | |
| 5,824,093 A | 10/1998 | Ray et al. | |
| 5,824,094 A | 10/1998 | Serhan et al. | |
| 5,836,948 A | 11/1998 | Zucherman et al. | |
| 5,865,848 A | 2/1999 | Baker | |
| 6,001,130 A | 12/1999 | Bryan et al. | |
| 6,045,579 A | 4/2000 | Hochshuler et al. | |
| 6,068,630 A | 5/2000 | Zucherman et al. | |
| 6,087,553 A | 7/2000 | Cohen et al. | |
| 6,113,637 A | 9/2000 | Gill et al. | |
| 6,126,689 A | 10/2000 | Brett | |
| 6,162,252 A | 12/2000 | Kuras et al. | |
| 6,176,882 B1 | 1/2001 | Biedermann et al. | |
| 6,332,894 B1 | 12/2001 | Stalcup et al. | |
| 6,387,130 B1 | 5/2002 | Stone et al. | |
| 6,395,032 B1 | 5/2002 | Gauchet | |
| 6,413,278 B1 | 7/2002 | Marchosky | |
| 6,447,448 B1 | 9/2002 | Ishikawa et al. | |
| 6,468,310 B1 | 10/2002 | Ralph et al. | |
| 6,475,639 B2 | 11/2002 | Shahinpoor et al. | |
| 6,565,605 B2 | 5/2003 | Goble et al. | |
| 6,582,466 B1 | 6/2003 | Gauchet | |
| 6,595,998 B2 | 7/2003 | Johnson et al. | |
| 6,620,196 B1 | 9/2003 | Trieu | |
| 6,626,943 B2 | 9/2003 | Eberlein et al. | |
| 6,645,248 B2 | 11/2003 | Casutt | |
| 6,733,535 B2 | 5/2004 | Michelson | |
| 6,770,094 B2 | 8/2004 | Fehling et al. | |
| 6,770,095 B2 | 8/2004 | Grinberg et al. | |
| 6,835,208 B2 | 12/2004 | Marchosky | |
| 7,326,248 B2 | 2/2008 | Michelson | |
| 7,503,920 B2 | 3/2009 | Siegal | |
| 7,655,010 B2 | 2/2010 | Serhan et al. | |
| 7,703,727 B2 | 4/2010 | Selness | |
| 7,731,751 B2 | 6/2010 | Butler et al. | |
| 7,799,081 B2 | 9/2010 | McKinley | |
| 7,837,734 B2 | 11/2010 | Zucherman et al. | |
| 7,850,733 B2 | 12/2010 | Baynham et al. | |
| 7,918,874 B2 | 4/2011 | Siegal | |
| 8,016,859 B2 | 9/2011 | Donofrio et al. | |
| 8,105,382 B2 | 1/2012 | Olmos et al. | |
| 8,262,666 B2 | 9/2012 | Baynham et al. | |
| 8,267,939 B2 | 9/2012 | Cipoletti et al. | |
| 8,343,193 B2 | 1/2013 | Johnson et al. | |
| 8,366,777 B2 | 2/2013 | Matthis et al. | |
| 8,579,981 B2 | 11/2013 | Lim et al. | |
| 8,636,802 B2 | 1/2014 | Serhan et al. | |
| 9,402,654 B2 | 8/2016 | Serhan | |
| 2001/0018614 A1 | 8/2001 | Bianchi | |
| 2002/0039620 A1 | 4/2002 | Shahinpoor et al. | |
| 2003/0028251 A1 | 2/2003 | Mathews | |
| 2003/0039620 A1 | 2/2003 | Rodriguez et al. | |
| 2003/0135275 A1 | 7/2003 | Garcia et al. | |
| 2003/0135277 A1 | 7/2003 | Bryan et al. | |
| 2003/0139812 A1 | 7/2003 | Garcia et al. | |
| 2004/0002761 A1 | 1/2004 | Rogers et al. | |
| 2004/0049188 A1 | 3/2004 | Slivka et al. | |
| 2004/0087947 A1 | 5/2004 | Lim et al. | |
| 2004/0193273 A1 | 9/2004 | Huang | |
| 2004/0243238 A1 | 12/2004 | Arnin et al. | |
| 2004/0249462 A1 | 12/2004 | Huang | |
| 2005/0119752 A1 | 6/2005 | Williams et al. | |
| 2005/0203624 A1 | 9/2005 | Serhan et al. | |
| 2006/0004431 A1 | 1/2006 | Fuller et al. | |
| 2006/0122701 A1 | 6/2006 | Kiester | |
| 2006/0142858 A1 | 6/2006 | Colleran et al. | |
| 2007/0272259 A1 | 11/2007 | Allard et al. | |
| 2012/0310352 A1 | 12/2012 | DiMauro et al. | |
| 2014/0107704 A1 | 4/2014 | Serhan et al. | |
| 2015/0374992 A1 | 12/2015 | Crosby et al. | |
| 2016/0000476 A1 | 1/2016 | Serhan et al. | |
| 2016/0249958 A1 | 9/2016 | Serhan et al. | |
| 2016/0249959 A1 | 9/2016 | Serhan et al. | |
| 2016/0331415 A1 | 11/2016 | Serhan et al. | |

OTHER PUBLICATIONS

U.S. Appl. No. 10/793,967, filed Mar. 6, 2004, Dynamized Interspinal Implant.
U.S. Appl. No. 14/134,090, filed Dec. 19, 2013, Dynamized Interspinal Implant.
U.S. Appl. No. 14/845,687, filed Sep. 4, 2015, Dynamized Interspinal Implant.
U.S. Appl. No. 15/148,937, filed May 6, 2016, Dynamized Interspinal Implant.
U.S. Appl. No. 15/149,085, filed May 7, 2016, Dynamized Interspinal Implant.

* cited by examiner

DYNAMIZED INTERSPINAL IMPLANT

CROSS-REFERENCE TO RELATED APPLICATIONS

This application is a continuation of U.S. application Ser. No. 15/149,085, filed on May 7, 2016, which is a continuation of U.S. application Ser. No. 15/148,937, filed on May 6, 2016, which is a continuation of U.S. application Ser. No. 14/845,687, filed on Sep. 4, 2015, which is a continuation of U.S. application Ser. No. 14/134,090, filed on Dec. 19, 2013 (now abandoned), which is a division of U.S. application Ser. No. 10/793,967, filed on Mar. 6, 2004 (now U.S. Pat. No. 8,636,802), each of which is hereby incorporated by reference in its entirety.

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint.

In some cases, when a patient having a collapsed disc moves in extension (e.g., leans backward), the posterior portion of the annulus fibrosis or folding of the ligamentum flavum may further compress and extend into the spinal canal. This condition, called "spinal stenosis", narrows the spinal canal and causes impingement of tissue upon the spinal cord, thereby producing pain.

There have been numerous attempts to provide relief for these afflictions by providing a spacer that inserts between adjacent spinous processes present in the posterior portion of the spinal column. This spacer essentially lifts the upper spinous process off of the lower spinous process, thereby relieving stenosis. In general, these interspinous implants are adapted to allow flexion movement in the patient, but resist or limit extension.

U.S. Pat. No. 6,068,630 ("Zuchermann") discloses a spinal distraction implant that alleviates pain associated with spinal stenosis by expanding the volume in the spinal canal or neural foramen. Zuchermann discloses a plurality of implants having a body portion and lateral wings. The body portion is adapted to seat between the adjacent spinous processes, while the wings are adapted to prevent lateral movement of the body portion, thereby holding it in place between the adjacent spinous processes.

U.S. Pat. No. 5,645,599 ("Samani") attempts to relieve spinal stenosis by essentially inserting a flexible horseshoe-shaped device between the adjacent spinous processes. Although the Samani device desirably provides a self-limiting flexibility, it nonetheless suffers from some inadequacies. For example, the Samani device does not provide for natural physiologic rotational movement, nor for post-operative adjustment. In addition, the Samani device discloses the insertion of a bearing cushion, and the adhesive bonding of the bearing cushion to the horseshoe element. However, it is believed that mere adhesive bonding of these elements would cause the cushion to be prone to migration.

SUMMARY OF THE INVENTION

The present inventors have developed a number of flexible interspinous devices having a number of desirable features providing improved performance over conventional solutions.

In a first embodiment, the device has a flexible anterior wall having a narrowed portion. The narrowed portion allows the device to twist in response to spinal rotation, thereby more closely mimicking natural physiologic movement.

Therefore, in accordance with the first embodiment of the present invention, there is provided an interspinous implant for insertion between adjacent spinous processes, the implant comprising:
a) a flexible body comprising:
  i) an upper posterior portion having an upper surface adapted to bear upon an upper spinous process,
  ii) a lower posterior portion having a lower surface adapted to bear upon a lower spinous process, and
  iii) an arcuate, flexible anterior wall connecting the upper and lower portions,
wherein the anterior wall has a narrowed portion.

In a second embodiment, the device has a cushion portion interdigitated with each of the upper and lower bearing portions. Because the cushion portion is interdigitated with these elements, a tenacious bond is provided and migration concerns are alleviated.

Therefore, in accordance with the second embodiment of the present invention, there is provided an interspinous implant for insertion between adjacent spinous processes, the implant comprising:
a) a flexible body comprising:
  i) an upper posterior portion having an upper surface adapted to bear upon an upper spinous process,
  ii) a lower posterior portion having a lower surface adapted to bear upon a lower spinous process,
  iii) an arcuate, flexible anterior wall connecting the upper and lower portions, and
b) a cushion element having an upper surface and a lower surface,
wherein the lower surface of the upper portion of the flexible body comprises a porous coating thereon, and wherein the upper surface of the cushion element is interdigitated with the porous coating.

In a third embodiment, the device is adapted to be post-operatively adjustable. The adjustability allows the device to respond to an altered physiologic state, such as an increased collapse of the disc space or decreased patient flexibility, by adjusting the overall stiffness of the implant.

Therefore, in accordance with the third embodiment of the present invention, there is provided an interspinous implant for insertion between adjacent spinous processes, the implant comprising:
  a) a flexible body comprising:
  i) an upper posterior portion having an upper surface adapted to bear upon an upper spinous process,
  ii) a lower posterior portion having a lower surface adapted to bear upon a lower spinous process,
  iii) an arcuate, flexible anterior wall connecting the upper and lower posterior portions, and
  iv) means for adjusting the stiffness of the implant.

DETAILED DESCRIPTION OF THE FIGURES

Figure 6:
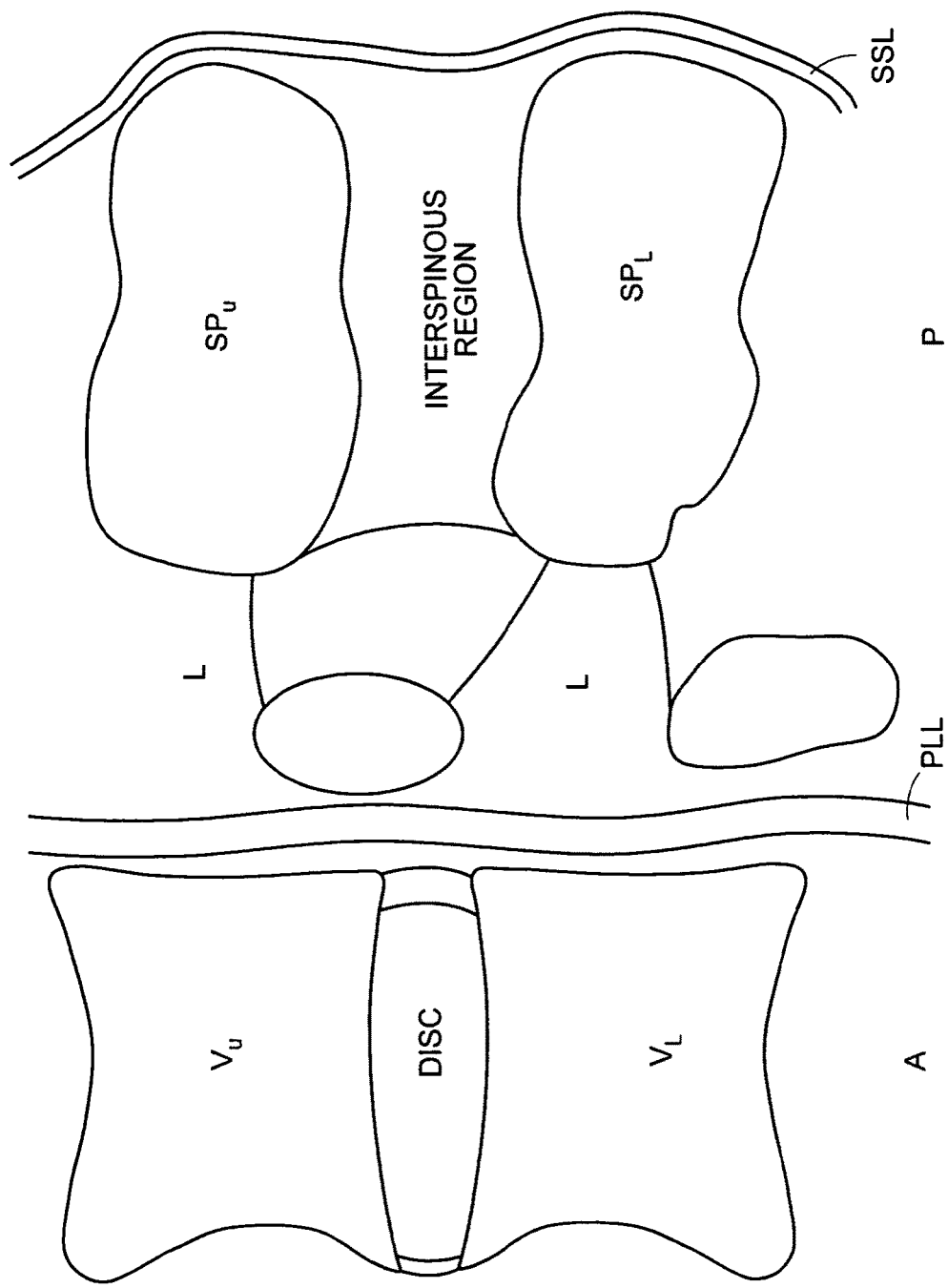
FIG. 6 is a side view of a functional spinal unit of the human anatomy.

For the purposes of the present invention, the term "interspinous" refers to the volume located between two adjacent spinous processes of adjacent vertebrae. The terms "anterior" and "posterior" are used as they are normally used in spinal anatomy. Accordingly, the "anterior" portion of the interspinous device is that portion rests relatively close to the spinal cord, while the "posterior" portion of the interspinous device is that portion rests relatively close to the skin on the patient's back. Now referring to FIG. 6, there is provided an anatomic "functional spinal unit" or FSU comprising an upper vertebrae Vu having an upper vertebral body $VB_U$ and an upper spinous process SPu, a lower vertebra having a lower vertebral body $VB_L$ having a lower spinous process $SP_L$. The vertebral bodies lies in the anterior A portion of the FSU, while the spinous processes lie in the posterior portion P of the FSU. Disposed between the vertebral bodies is a disc space DISC. Disposed between the spinous process is an "interspinous region". Disposed between the spinous process and the vertebral body of each vertebra is a lamina L. The supraspinous ligament SSL lies posterior to the spinous processes. The Posterior longitudinal ligament PLL lies posterior to the vertebral bodies.

Figure 1A:
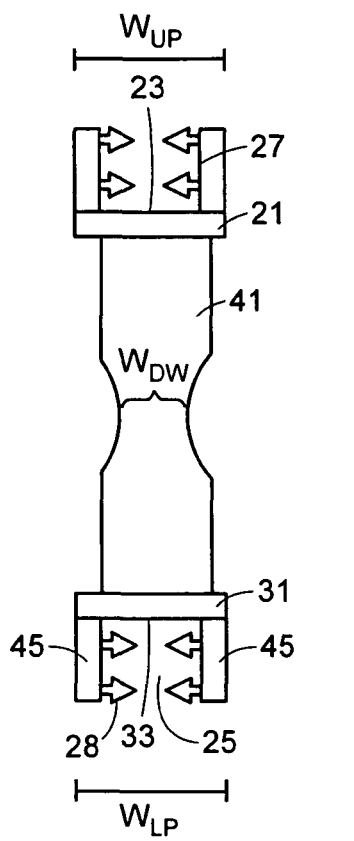
FIG. 1a is a posterior view of the first embodiment of the interspinous implant in the coronal plane
Figure 1B:
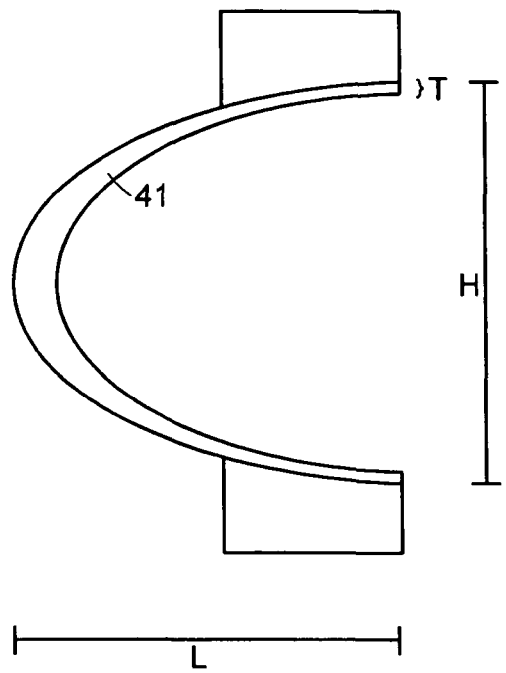
FIG. 1b is a side view of the first embodiment of the interspinous implant in the saggital plane.

Now referring to FIGS. 1a and 1b, there is provided an interspinous implant 1 for insertion between adjacent spinous processes, the implant comprising:
  a) a flexible body 11:
  i) an upper posterior portion 21 having an upper surface 23 adapted to bear upon an upper spinous process and a width $W_{UP}$,
  ii) a lower posterior portion 31 having a lower surface 33 adapted to bear upon a lower spinous process and a width $WL_P$, and
  iii) a flexible arcuate anterior wall 41 connecting the upper and lower portions and having a narrowed portion 43 defining a minimum width $W_{DW}$,
wherein the minimum width of the anterior wall is less than the width $W_{UP}$ of the upper portion.

Figure 1C:
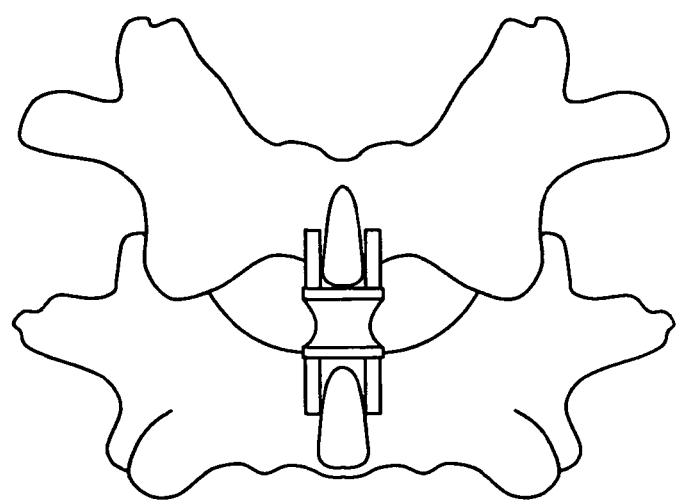
FIG. 1c is a posterior view of the first embodiment of the interspinous implant implanted between adjacent vertebrae.

Now referring to FIG. 1c, in use, the implant of FIGS. 1a and 1b is inserted into the interspinous region of an functional spinal unit (FSU), that is, between the adjacent spinous processes. The U-shaped body has a stiffness and geometry adapted to provide the desired spacing between the upper and lower process. In addition, in preferred embodiments, the U-shaped body is adapted to be somewhat flexible, so that it somewhat restricts the extent of extension motion of the FSU.

In preferred embodiments, the flexible body is U-shaped. In other embodiments, the flexible body has a posterior wall (preferably, arcuate) that flexibly connects the posterior portions of the upper and lower bearing surfaces of the flexible body to provide an overall substantially oval shape.

Preferably, the flexible body has a configuration and is made of a material that provides a first stiffness that limits the range of motion of the FSU. In some embodiments, the flexible body stiffness provides at least 50% of the overall initial stiffness of the implant, preferably at least 75%, more preferably at least 90%.

Preferably, the flexible body is adapted to provide a stiffness of between 50 N/mm and 1000 N/mm, more preferably between 100 N/mm and 500 N/mm. When the flexible body stiffness is in this range, it maintains the flexion/extension ROM of a normal lumbar FSU to less than 20 degrees, with less than 13 degrees of motion in flexion and less than 7 degrees of motion in extension. Preferably, the typical displacement of the posterior ends of the device under physiologic loading in the saggital plane is in the range of 1-6 mm.

The flexible can be made of a suitable biocompatible material typically used in structural spinal applications, including metals, plastics and ceramics. In some embodiments, the flexible body is made of a material selected from the group consisting of titanium alloy (including memory metals and superelastic alloys), stainless steel, and chrome cobalt. Preferably, the flexible body is provided in a sterile form.

Now referring to FIG. 1, in some embodiments, the flexible body has a height H of between 10 mm and 20 mm; a thickness T of between 1 mm and 2 mm; a length L of between 20 mm and 30 mm, and a width W of between 3 and 20 mm, preferably between 5 mm and 10 mm. In these embodiments, the implant can be easily inserted between typical adjacent spinous processes.

In some embodiments, the flexible body has a longitudinal cross section having a horseshoe shape. In others, the longitudinal cross-section describes a circle. In others, it is a pill shape. In others, it is substantially oval. In some embodiments, the upper and lower posterior portions are substantially non-parallel.

In some embodiments, as shown in FIG. 1b, the upper and lower posterior portions of the flexible body each have a longitudinal recess 25 defining a bearing surface 23, 33 and opposing recess walls 27. The recess shape is adapted to receive projecting portions of the opposed spinous processes, thereby securing the U-shaped shell between the spinous processes. In some embodiments, the recess walls have teeth 28 extending inwardly therefrom that provide a more grip upon the spinous processes. In some embodiments, at least the bearing surfaces of the recess have teeth 415 (as shown in FIG. 4c) extending outwardly therefrom that provide a more grip upon the spinous processes.

In some embodiments, the recess 25 defines an upper pair of extensions 45 extending from the bearing surface 33 and collectively defining a bracket. Each extension may comprise a transverse throughhole (not shown) adapted for fixing the implant to the adjacent spinous processes.

In some embodiments, each extension comprises a transverse throughhole adapted for fixing the implant to the adjacent spinous processes. In some embodiments, the implant further comprises a fastening element having a first end extending through the first transverse throughole and a second end extending through the second transverse through-hole.

The flexible body of the present invention preferably has a flexible anterior wall connecting the upper and lower portions of the U-shaped body, thereby providing a spring quality to the U-shaped body for flexibly resisting extreme FSU extension. This flexible anterior wall is preferably shaped to conform with the opposed surfaces of the opposing spinous processes (as shown in FIG. 1c). This quality also insures the grip of the implant and reduces unwanted stresses upon the flexible body. In some embodiments, the thickness of the distal wall is greater than the thickness of the posterior portions.

Figure 2A:
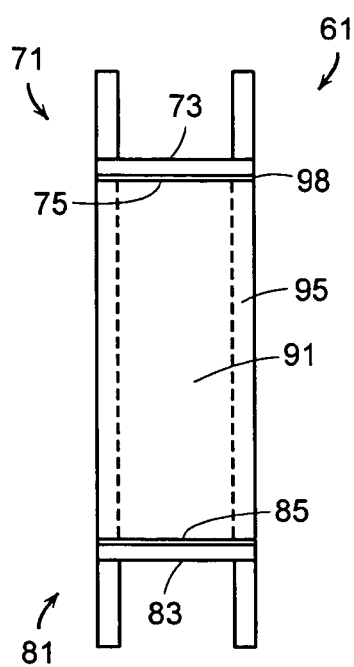
FIG. 2a is a posterior view of the second embodiment of the interspinous implant.
Figure 2B:
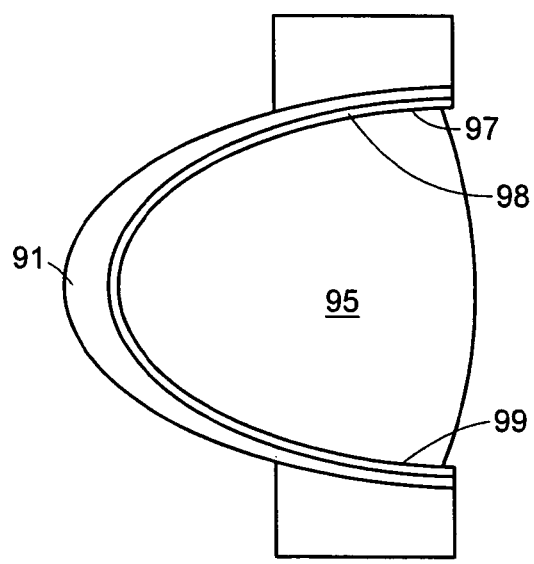
FIG. 2b is a side view of the second embodiment of the interspinous implant in the saggital plane.

Now referring to FIGS. 2a and 2b, there is provided an interspinous implant 51 for insertion between adjacent spinous processes, the implant comprising:
a) a flexible U-shaped body 61:
  i) an upper portion 71 having an upper surface 73 adapted to bear upon an upper spinous process and a lower surface 75,
  ii) a lower portion 81 having a lower surface 83 adapted to bear upon a lower spinous process and an upper surface 85,
  iii) a flexible distal wall 91 connecting the upper and lower portions, and
b) a cushion element 95 having an upper surface 97 and a lower surface 99,
wherein the lower surface of the upper portion of the flexible body comprises a porous coating 98 thereon, and wherein the upper surface of the cushion element is interdigitated with the porous coating.

In use, the cushion element provides a dampening effect upon natural extension. The interdigitated nature of the cushion bond reduces migration concerns.

In some embodiments, the bonding covers substantially the entire extent of the inner surface of the U-shaped body (i.e., the upper surface of the cushion is bonded to the lower surface of the upper posterior portion, the anterior surface of the cushion is bonded to the posterior surface of the flexible anterior wall, and the lower surface of the cushion is bonded to the upper surface of the lower posterior portion).

Figure 2C:
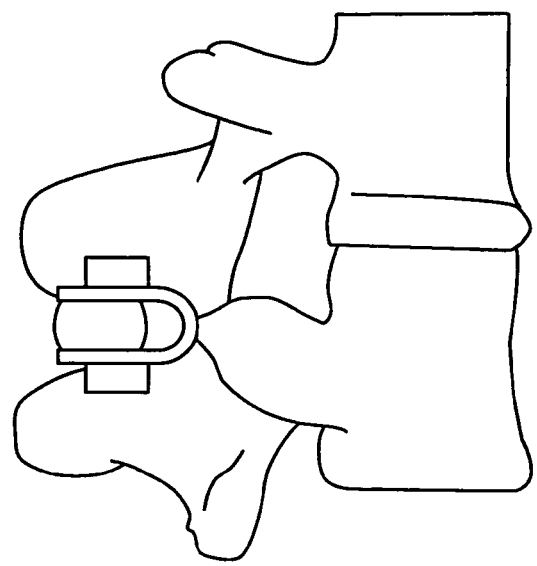
FIG. 2c is a side view of an embodiment of the interspinous implant implanted between adjacent vertebrae.

Now referring to FIG. 2c, in some embodiments, the bonding covers only the posterior portions of the inner surface of the U-shaped body (i.e., the lower surface of the upper posterior portion, and the upper surface of the lower posterior portion, but not the posterior surface of the flexible anterior wall). The partial coverage of this embodiment provides an amount of stress relief to the cushion-U-shaped body interface.

The cushion element of FIGS. 2a-2b is preferably made of an elastomeric material, more preferably a polyolefin rubber or carbon black reinforced polyolefin rubber. The hardness of the elastomeric cushion element is preferably between 56 and 72 shore A durometer. The ultimate tensile strength of the cushion element is preferably greater than 1600 psi. The cushion element preferably has an ultimate elongation greater than 300% using the ASTM D412-87 testing method, and a tear resistance greater than 100 psi using the ASTM D624-86 testing method. Although the cushion element is preferably a polyolefin rubber, it can be made of any elastomeric material that simulates the response of the natural ligaments.

Still referring to FIG. 2a, a porous coating 98 is provided as the inner surface of the U-shaped body. The porous coating provides an opportunity for the cushion element to interdigitate with the porous coating, and so obtain a greater amount of surface contact between the U-shaped body and the cushion, thereby achieving a lower maximum stress. In some embodiments, the coating covers the entire extent of the inner surface of the U-shaped body (i.e., the upper surface of the cushion is bonded to the lower surface of the upper posterior portion, the anterior surface of the cushion is bonded to the posterior surface of the flexible anterior wall, and the lower surface of the cushion is bonded to the upper surface of the lower posterior portion). Preferably, the coating comprises a layer of small spherical particles or beads.

In some embodiments, the coating covers only the posterior portions of the inner surface of the U-shaped body (i.e., the lower surface of the upper posterior portion, and the upper surface of the lower posterior portion, but not the posterior surface of the flexible anterior wall).

In some embodiments, a coating may also be applied to the superior side of the upper portion and the inferior side of the lower portion to promote bony ingrowth and osteointegration. In some embodiments thereof, and the coating may include beads, and may have osteobiologic components such as hydroxyapatite or tricalcium phosphate.

The present inventors have noted that there may be a need to correct the range of motion (ROM) provided by a motion disc after the motion disc has been implanted and there is need to change the load transferred through the facet joints to alleviate pain and facet joint degeneration.

For example, because implantation of spinal prostheses is an inexact procedure, there may be times when implantation provides too much or too little motion. For example, in some implantation procedures, damage to the anterior longitudinal ligament (ALL) is contemplated. Because the ALL in its physiologic form restricts the flexion/extension range of the natural disc, damage to it may provide the implanted disc with an unacceptably large range of motion (ROM) in flexion and extension. This overly large ROM is problematic because it produces atypical loads upon the facet joints as well as the adjacent intervertebral discs, thereby leading to premature degeneration of those facet joints and intervertebral discs. Accordingly, there may be a need to post-operatively correct the ROM of the implant in order to fine tune the ROM.

In another example, an implanted disc has an acceptable ROM at the time of implantation, but the patient undergoes typical aging so that the patient's normal range of motion decreases over time. In this case, it may be desirable to decrease the implant ROM so that it corresponds with the patient's natural decreased ROM.

Accordingly, there may be a need to post-operatively correct the ROM of the implant in order to adjust the implant ROM to the new needs of the patient.

The implant of the present invention is advantageous because it can be inserted into the spine at a first stiffness, and then adjusted to a second stiffness to meet the needs of the particular patient.

In a first preferred embodiment, the stiffness of the implant is adjusted post-operatively in order to fine tune the implant to the surgical needs of the patient.

In a second preferred embodiment, the stiffness of the implant is adjusted in order to fine tune the implant to the changing post-surgical needs of the patient.

In many embodiments, the stiffness of the implant is increased in order to reduce the ROM of a functional spinal unit (FSU).

Figure 3A:
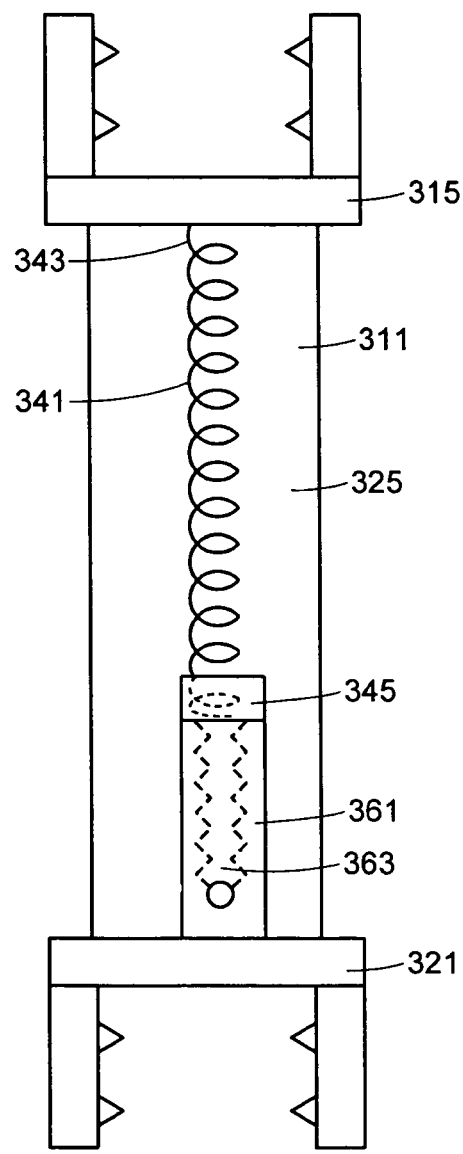
FIG. 3a is a posterior view of the third embodiment of the interspinous implant.
Figure 3B:
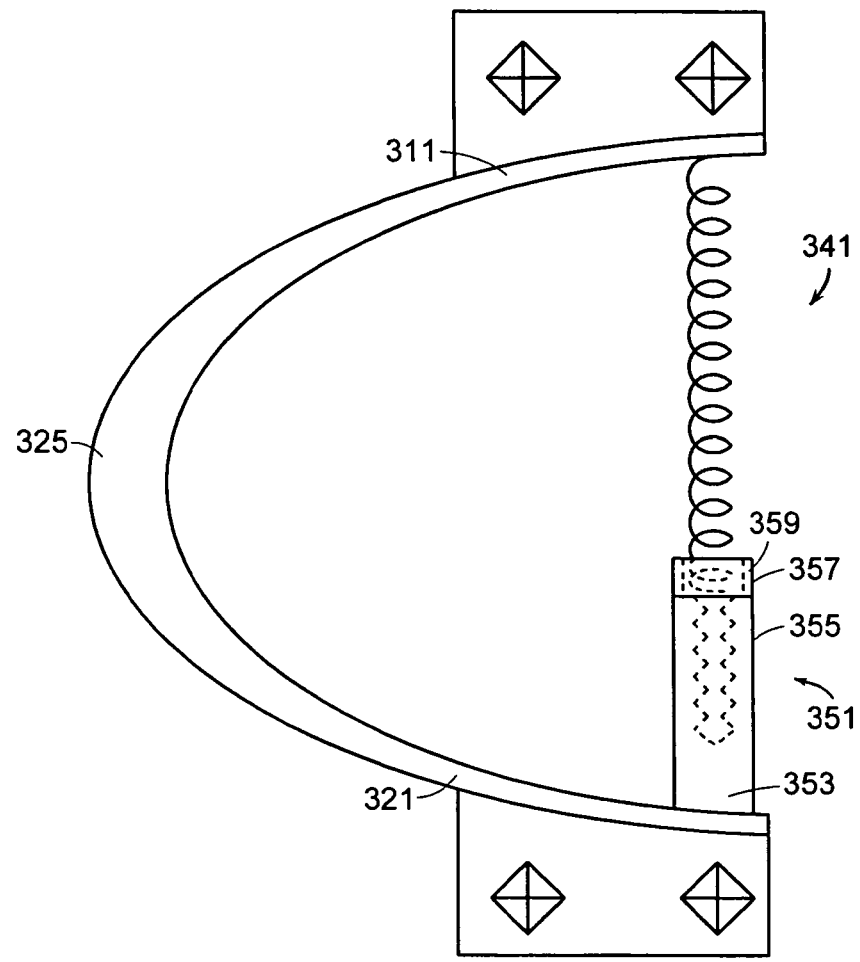
FIG. 3b is a side view of the third embodiment of the interspinous implant in the saggital plane.

In some embodiments, the implant further comprises a compression spring, and the overall stiffness of the implant is changed by adjusting the length of the compression spring. Now referring to FIGS. 3a-3b, in some embodiments, there is provided an interspinous implant 301 for insertion between adjacent spinous processes, the implant comprising:

a) a flexible outer shell 311 comprising:
  i) an upper posterior portion 315 adapted to bear upon an upper spinous process,
  ii) a lower posterior portion 321 adapted to bear upon a lower spinous process,
  iii) a flexible anterior wall 325 connecting the upper and lower posterior portions,
b) a compression spring 341 having an upper portion 343 and a lower portion 345, the upper portion of the compression screw being attached to the upper posterior portion of the flexible outer shell, and
c) a worm screw 351 having a lower portion 353 connected to the lower posterior portion and an upper portion 355 contacting the lower portion of the compression spring.

In this particular embodiment, the upper portion of the worm screw comprises a cup 357 having an annular sidewall 359 extending upward. The lower end portion of the compression spring is not rigidly attached to the cup, but rather sits freely in the annulus and bears against the cup. Containment by the cup allows the upper end of the worm screw to simply bear against the lower end of the spring without requiring rigid connection thereto.

In use, actuation of the worm screw causes inner thread 363 of the worm screw to turn relative to the outer cylinder 361 of the worm screw. The outer cylinder 361 responds by moving axially upward, thereby forcing compression of the compression spring, and increasing the effective resistance of the device to axial compression.

Figure 4A:
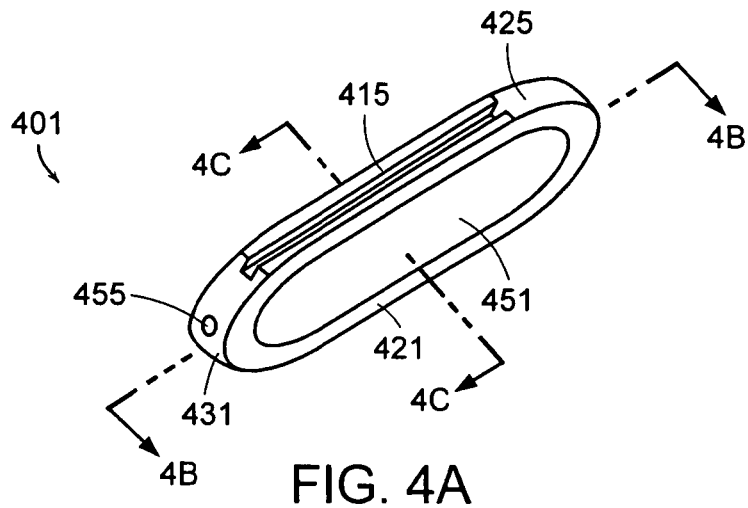
FIGS. 4a-4c are perspective, longitudinal and frontal cross-sectional views of a fourth embodiment of the present invention.
Figure 4B:
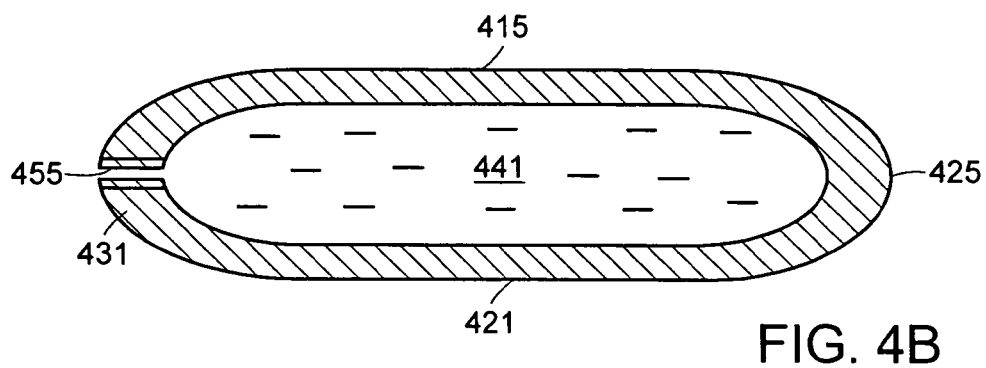
Figure 4C:
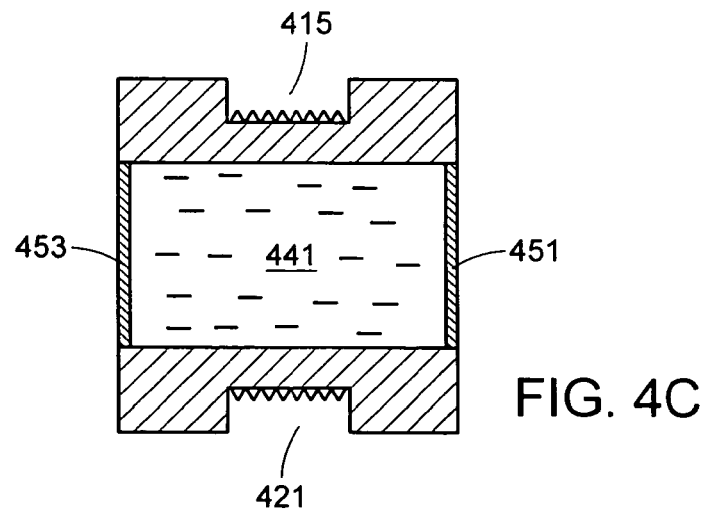
Figure 4D:
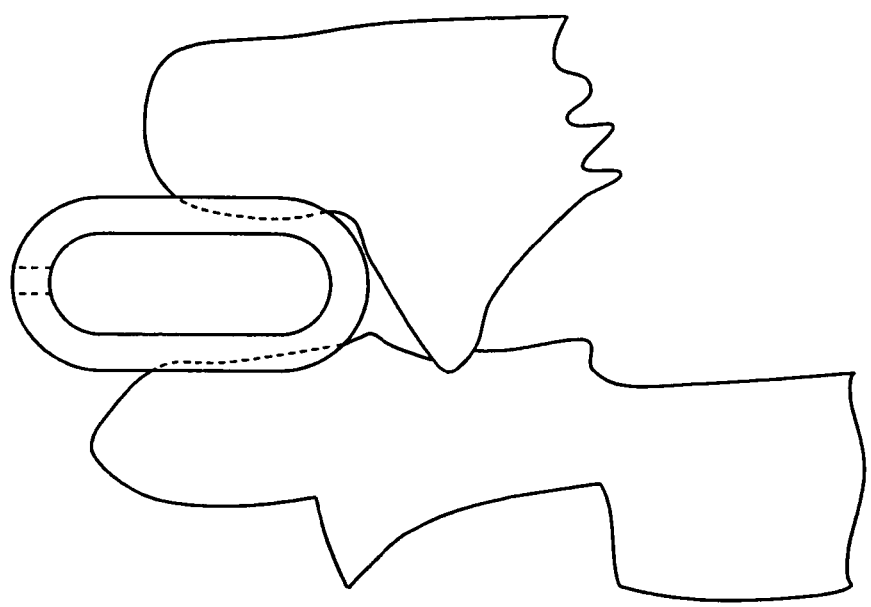
FIG. 4d is a side view of the fourth embodiment of the interspinous implant implanted between adjacent vertebrae.

Now referring to FIGS. 4a-4c, in some embodiments, there is provided an interspinous implant 401 for insertion between adjacent spinous processes, the implant having an implant stiffness and comprising:

a) a flexible outer shell 411 having a shell stiffness and comprising:
  i) an upper surface 415 adapted to bear upon an upper spinous process,
  ii) a lower surface 421 adapted to bear upon a lower spinous process,
  iii) an arcuate anterior wall 425 connecting the upper and lower surfaces, and
  iv) an arcuate posterior wall 431 extending between the upper and lower surfaces,
b) compliant side walls 451,453, extending between the upper and lower surfaces, and
c) an inner core 441 (such as a hydrogel) contained within the shell, wherein the inner core has an adjustable stiffness.

When it is desired to decrease the range of motion ("ROM") of the functional spinal unit ("FSU"), the stiffness of the core material may be increased, thereby increasing the stiffness of the implant and its resistance to an axial load. The resulting increase in the stiffness of the interspinous implant provides a more substantial resistance to extension, thereby desirably decreasing the ROM of the FSU to correspond with the needs of the patient.

Similarly, when it is desired to increase the range of motion ("ROM") of the functional spinal unit ("FSU"), the stiffness of the core material is decreased, thereby decreasing the stiffness of the implant and its resistance to an axial load. The resulting decrease in the stiffness of the interspinous implant reduces resistance to extension, thereby desirably increasing the ROM of the FSU to correspond with the needs of the patient.

The implant of this embodiment of the present invention also has a flexible posterior wall extending between the upper and lower portions of the U-shaped body. This posterior wall is preferably arcuate and preferably connects the upper surface of the lower portion and the lower surface of the upper portion of the U-shaped body to form a substantially oval body (as shown). In this condition, the posterior wall provides substantial closure to the U-shaped body. Accordingly, adjustment of the stiffness of the core material residing within the outer shell increases or decreases the stiffness of the implant.

The compliance of the sidewalls is selected to correspond with the level of resistance desired by the implant. For example, in some embodiments (as in FIG. 4a-4c,) the sidewalls are very thin and may be made of a very flexible material, such as a plastic weave. In these embodiments, the high compliance of the sidewalls will allow the core material to bulge laterally in response to an axial load, thereby tempering the resistance provided by the core material to the axial load.

In other embodiments, however, the sidewalls can be made of metal, and even be integral with the outer shell. In these embodiments, the sidewalls will be flexible but more rigid than a plastic membrane. In these embodiments, the relative rigidity of the sidewalls will not allow the core material to bulge significantly laterally, thereby augmenting the resistance provided by the core material to the axial load.

Preferably, the core is a fluid material contained within the cavity of the shell and is made of a material having a quality whose adjustment will produce a change in the stiffness of the implant. When the stiffness of the core is adjusted, the overall stiffness of the implant correspondingly changes. In some embodiments, the core has a first stiffness and contributes between 10 and 20% of the overall initial stiffness of the implant. In such embodiments, the stiffness of the core is increased to a second stiffness that increases the overall initial stiffness of the implant up to at least 40% to provide an adjusted implant stiffness of at least 300 N/mm, and more preferably at least 500 N/mm. When the implant stiffness is in this range, the implant can by itself provide sufficient stiffness to reduce the extension of a normal lumbar FSU to less than 7 degrees, preferably less than 5 degrees.

Preferably, the core material is selected to be sensitive to an external stimulus, which, when applied, stimulates the core material to adjust its stiffness from a first stiffness to a second stiffness. In some embodiments, the stimulus stimulates the core to increase its stiffness. In some embodiments, the stimulus stimulates the core to lower its stiffness.

Preferably, the core material is sensitive to a stimulus selected from the group consisting pH, light, and electric current.

In preferred embodiments, the core material comprises a hydrogel. In preferred embodiments, the hydrogel undergoes expansion when stimulated by a decreased pH. The resulting expansion of the core material increases the stiffness of the core, thereby increasing the stiffness of the implant and providing increased resistance to extension by the FSU. In some embodiments, the hydrogel is selected from ionic polymers disclosed in US Published Patent Application No. 2002/0039620, the specification of which is incorporated by reference in its entirety. In some embodiments, the hydrogel is selected from ionic polymers disclosed in U.S. Pat. No. 6,475,639, the specification of which is incorporated by reference in its entirety.

When pH is selected as the stimuli, in some embodiments, an acid or a base is introduced into the core material from an ex vivo source. For example, the acid or base can be administered subcutaneously via a hypodermic needle and introduced into the core material through a fluid port 455. The provision of a fluid port provides the surgeon with the flexibility to selected the amount of acid or base needed to suit the needs of the patient.

In other embodiments in which pH is selected as the stimuli, the implant further comprises a container that individually houses and sequesters the acid or base from the core material. For example, the acid or base can be sequestered in a valved, separate compartment within the shell that is in fluid connection with the cavity housing the core material. The valve is opened (for example, by telemetry), the acid or base enters the cavity housing the core material and mixes with the core material. The resulting pH change causes a change in the specific volume of the core material, thereby increasing or decreasing the stiffness of the core material and the overall implant. The advantage of this embodiment is that the stiffness of the implant is changed through a completely non-invasive technique.

In some embodiments (not shown), the device could be made of a shape memory metal having a relatively flexible property during the martensitic phase and a relatively stiff property in the austenitic phase. In one embodiment, this memory metal device could be implanted in its flexible martensitic phase. If the clinician desires to increase the stiffness of the implant, the clinician could raise the temperature of the device (by heating) to a temperature above its austenitic phase, thereby increasing the stiffness of the device and increasing its resistance to an axial compressive load.

In some embodiments of the present invention, the implant further comprises smart features for helping the surgeon monitor and react to the changing conditions of the implanted device.

In some embodiments, a sensing means is also used with the implant of the present invention. This sensing means analyzes physical surroundings. Its purpose is to identify when a significant change has occurred which could warrant adjusting the stiffness of the implant. The sensor can be contained within the implant, or provided as a stand alone entity.

In some embodiments, a reporting means for reporting the findings of the sensors to an ex vivo source is also used with the implant of the present invention. The reporter can be contained within the implant, or provided as a stand alone entity.

In some embodiments, a receiver for receiving ex vivo-generated information is also used with the implant of the present invention. The receiver can be contained within the implant, or provided as a stand alone entity.

In some embodiments, the implant comprises two shells having flexible anterior walls extending in the same direction, wherein the stiffness is adjusted by adjusting the distance between the respective flexible anterior walls. Now referring to FIG. 5a, there is provided an interspinous implant 501 for insertion between adjacent spinous processes, the implant comprising:
   a) a flexible outer shell 511 comprising:
   i) an upper posterior portion 515 adapted to bear upon an upper spinous process and having a lower end 517 having a first set of teeth 519,
   ii) a lower posterior portion 521 adapted to bear upon a lower spinous process and having a upper end 522 having a second set of teeth 523,
   iii) a flexible anterior wall 525 connecting the upper and lower posterior portions of the flexible outer shell,
   b) a flexible inner shell 551 comprising:
   i) an upper posterior portion 555 having an upper end 556 having a third set of teeth 557 engaged in the first set of teeth,
   ii) a lower posterior portion 571 having a lower end 573 having fourth set of teeth 577 engaged in the second set of teeth,
   iii) a flexible anterior wall 575 connecting the upper and lower posterior portions.

Figure 5A:
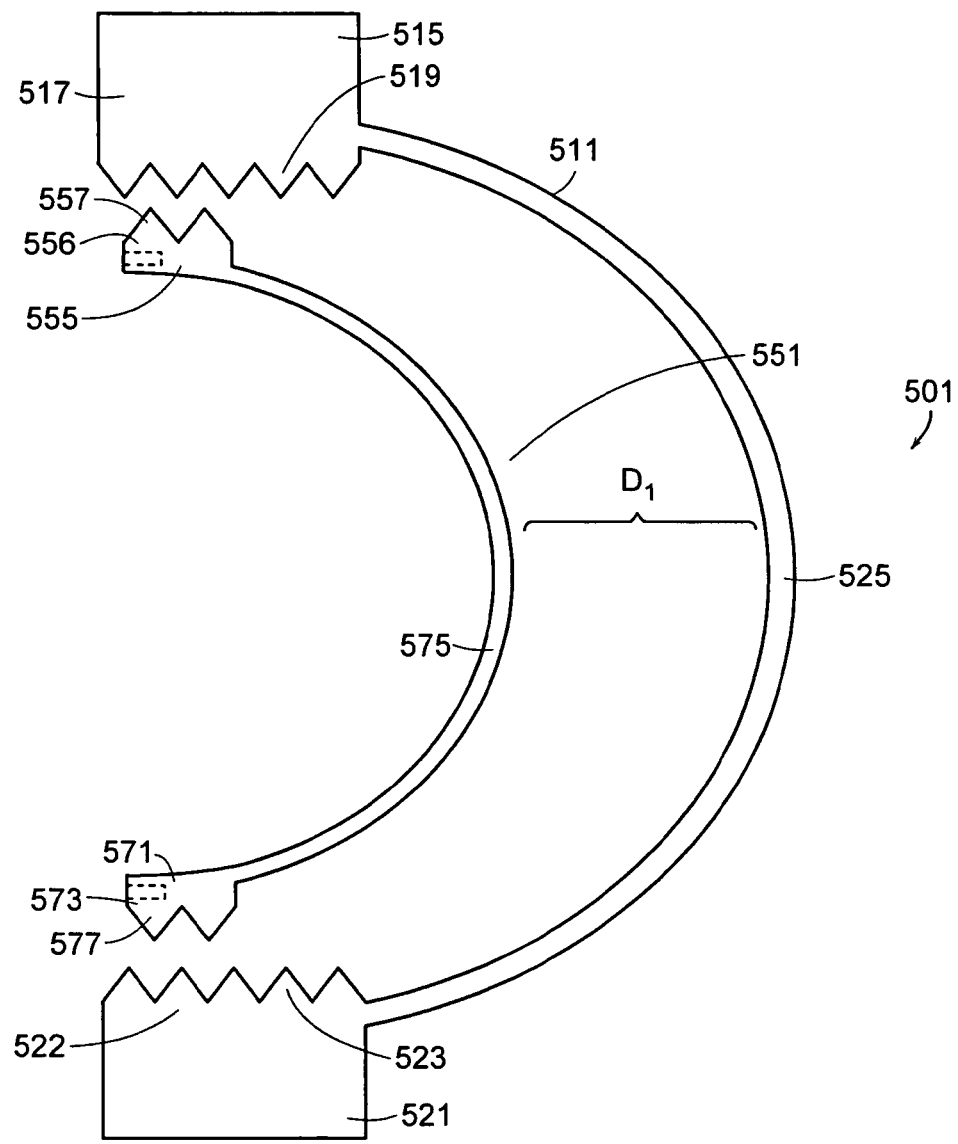
FIGS. 5a-b are side views of a fifth embodiment of the interspinous implant having outer and inner flexible shells.

In use, the implant of FIG. 5a is implanted into the interspinous void so that the opposing sets of teeth of the inner and outer shells are engaged to the opposed spinous processes, thereby providing a secure implant and defining a distance between the anterior walls $D_1$ of the inner and outer shells. If the clinician desires to change the stiffness of the implant, then the clinician may alter the distance D between the anterior walls of the inner and outer shells. Reducing the distance D between the anterior walls will cause a decrease in the stiffness of the implant, while increasing the distance D between the anterior walls will cause an increase in the stiffness of the implant.

Figure 5B:
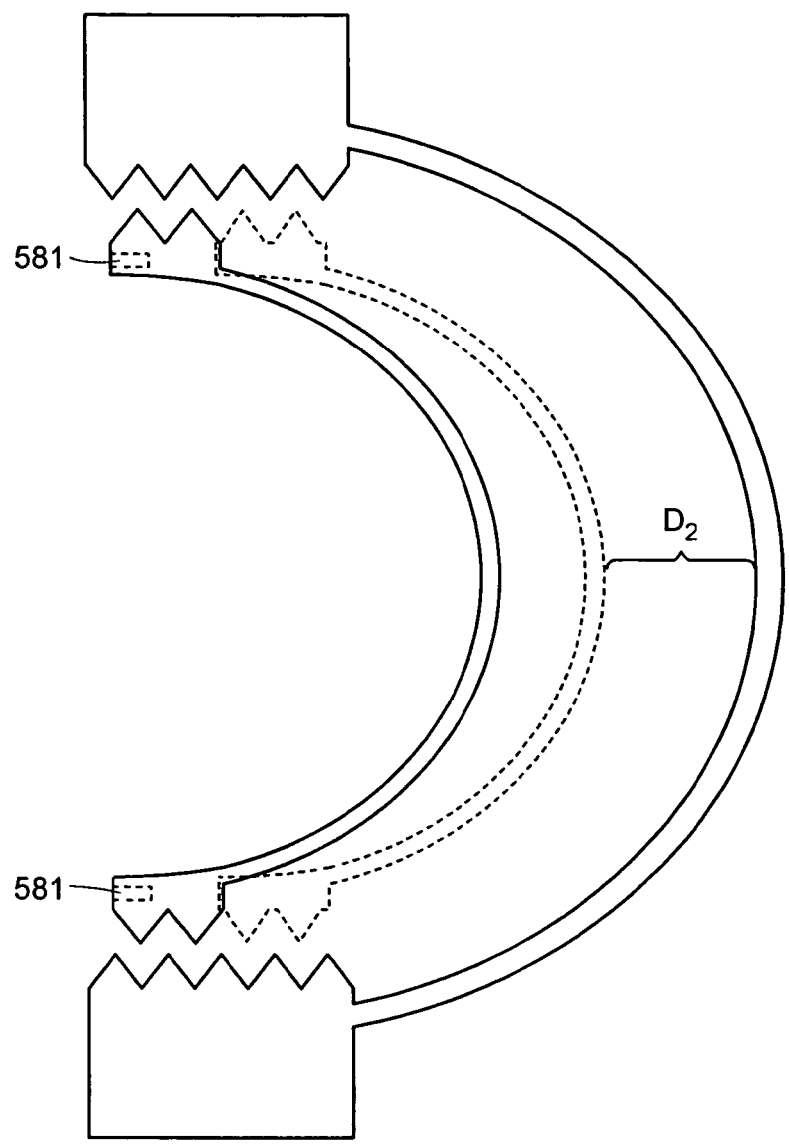

Now referring to FIG. 5b, when the clinician desires to decrease the stiffness of the implant of FIG. 5a, the clinician can use a pair of forceps (not shown) to engage the slots 581 provided on the upper and lower posterior portions of the inner shell. Providing a clamping force through the forceps squeezes together the posterior portions of the inner shell, thereby disengaging the respective pairs of teeth. The clinician can then move the disengaged inner shell anteriorly by a predetermined distance to a second position (shown in shadow), thereby decreasing the distance between the anterior walls to a smaller distance $D_2$ and lowering the stiffness of the implant.

In other embodiments, the slots of the implant of FIGS. 5a and 5b are replaced within other means for adjusting the distance D between the flexible anterior walls of the inner and outer shells. For example, in some embodiments, a set screw or a worm gear may be provided on the implant to alter the distance D, thereby adjusting the stiffness of the implant.

Therefore, in accordance with the present invention, there is provided an interspinous implant for insertion between adjacent spinous processes, the implant comprising:
   a) a flexible outer shell comprising:
   i) an upper posterior portion adapted to bear upon an upper spinous process and having a lower end having a first set of teeth,
   ii) a lower posterior portion adapted to bear upon a lower spinous process and having a upper end having a second set of teeth,
   iii) a flexible anterior wall connecting the upper and lower posterior portions of the flexible outer shell,
   b) a flexible inner shell comprising:
   i) an upper posterior portion having an upper end having a third set of teeth engaged in the first set of teeth,
   ii) a lower posterior portion having a lower end having fourth set of teeth engaged in the second set of teeth,
   iii) a flexible anterior wall connecting the upper and lower posterior portions.

In preferred embodiments, the implant of the present invention is used posteriorly in conjunction with a motion disc inserted within the disc space of the anterior portion of the spinal column. For example, in some embodiments, the implant of the present invention is used in conjunction with a motion disc having a large range of motion ("ROM"). Various motion discs are described by Stefee et al. in U.S. Pat. No. 5,071,437; Gill et al. in U.S. Pat. No. 6,113,637; Bryan et al. in U.S. Pat. No. 6,001,130; Hedman et al. in U.S.

Pat. No. 4,759,769; Ray in U.S. Pat. No. 5,527,312; Ray et al. in U.S. Pat. No. 5,824,093; Buttner-Janz in U.S. Pat. No. 5,401,269; and Serhan et al. in U.S. Pat. No. 5,824,094; all which documents are hereby incorporated herein by reference in their entireties. The flexibility of the flexible body provides resistance to extreme extension, thereby restricting the motion disc to a more narrow and more physiologically desirable range of motion.

Therefore, in accordance with the present invention, there is provided a kit for providing therapy to a functional spinal unit comprising an upper vertebrae having an upper spinous process, a lower vertebrae having a lower spinous process, and a disc space therebetween, the kit comprising:

a) an interspinous implant for insertion between adjacent spinous processes, the implant comprising a flexible (preferably, U-shaped) body comprising:
  i) an upper posterior portion having an upper surface adapted to bear upon an upper spinous process,
  ii) a lower posterior portion having a lower surface adapted to bear upon a lower spinous process, and
  iii) a flexible (preferably arcuate) anterior wall connecting the upper and lower portions, and
b) an artificial disc adapted for insertion into the disc space.

We claim:

1. An implant, comprising:
   a) a body portion having a first end, a second end, an upper portion having an upper surface adapted to bear upon an upper vertebra, and a lower portion having a lower surface adapted to bear upon a lower vertebra, wherein the body portion tapers substantially continuously posteriorly from the first end to the second end,
   b) a flange extending vertically from the lower portion,
   c) a screw extending into the flange, the screw having a longitudinal axis and a head portion, and
   d) a spring contacting the head portion of the screw, the spring having a longitudinal axis, wherein the longitudinal axis of the screw is substantially parallel to the longitudinal axis of the spring.

2. The implant of claim 1, wherein an end portion of the flange comprises a cup having a substantially annular sidewall.

3. The implant of claim 2, wherein the spring sits freely in and bears against the cup.

4. The implant of claim 1, wherein the body portion is monolithic.

5. The implant of claim 1, wherein a thickness of the body portion is greater at the first end than at the second end.

6. An implant, comprising:
   a) a body portion having a first end, a second end, an upper portion having an upper surface adapted to bear upon an upper vertebra, and a lower portion having a lower surface adapted to bear upon a lower vertebra, wherein the body portion tapers from the first end to the second end,
   b) a flange extending vertically from the upper or lower portion,
   c) a screw extending into the flange, and
   d) a spring contacting the screw, the spring being configured to expand and contract in a direction that is substantially perpendicular to an anterior-posterior axis extending between the first and second ends of the implant.

7. The implant of claim 6, wherein the spring is configured to expand and contract in a direction that is substantially parallel to a height direction between the upper and lower surfaces of the implant.

8. The implant of claim 6, wherein an end portion of the flange comprises a cup having a substantially annular sidewall.

9. The implant of claim 8, wherein the spring sits freely in and bears against the cup.

10. The implant of claim 6, wherein the flange extends from the lower portion.

11. The implant of claim 6, wherein the body portion is monolithic.

12. The implant of claim 6, wherein a thickness of the body portion is greater at the first end than at the second end.

13. A method of treating a spinal condition, comprising: implanting between adjacent vertebra an implant comprising:
   a) a body portion having an anterior end, a posterior end, an upper portion having an upper surface adapted to bear upon an upper vertebra and a lower portion having a lower surface adapted to bear upon a lower vertebra,
   b) a flange extending substantially vertically from the lower portion,
   c) a screw extending into the flange, and
   d) a spring contacting a head portion of the screw,
   wherein the implant is implanted in an orientation whereby the body portion tapers towards the spinal cord.

14. The method of claim 13, wherein the implant is implanted such that the spring substantially lies in a sagittal plane of the patient.

15. The method of claim 13, wherein the spring is configured to expand and contract in a sagittal plane of the patient.

16. The method of claim 13, wherein the body portion is monolithic.

17. The method of claim 13, wherein a thickness of the body portion is greater at the anterior end than at the posterior end.

* * * * *